United States Patent [19]

Schiraldi et al.

[11] Patent Number: 4,713,243

[45] Date of Patent: Dec. 15, 1987

[54] BIOADHESIVE EXTRUDED FILM FOR INTRA-ORAL DRUG DELIVERY AND PROCESS

[75] Inventors: Michael T. Schiraldi, East Brunswick, N.J.; Martin M. Perl, Brooklyn, N.Y.; Howard Rubin, Rockaway, N.J.

[73] Assignee: Johnson & Johnson Products, Inc., New Brunswick, N.J.

[21] Appl. No.: 874,904

[22] Filed: Jun. 16, 1986

[51] Int. Cl.$^4$ .................. A01N 59/10; A61K 33/16
[52] U.S. Cl. .................. 424/151; 424/449; 424/435
[58] Field of Search .......... 424/21, 28, 449, 435, 424/151

[56] References Cited

U.S. PATENT DOCUMENTS

| | | | |
|---|---|---|---|
| 4,292,299 | 9/1981 | Suzuki et al. | 424/16 |
| 4,421,738 | 12/1983 | Yamigawa et al. | 424/21 |
| 4,517,173 | 5/1985 | Kizawa et al. | 424/16 |

*Primary Examiner*—Peter F. Kulkosky

[57] ABSTRACT

A bioadhesive extruded single or multi-layered thin film, especially useful in intra-oral controlled-releasing delivery, having a water soluble or swellable polymer matrix bioadhesive layer which can adhere to a wet mucous surface and which bioadhesive layer consists essentially of 40-95% by weight of a hydroxypropyl cellulose, 5-60% of a homopolymer of ethylene oxide, 0-10% of a water-insoluble polymer such as ethyl cellulose, propyl cellulose, polyethylene and polypropylene, and 2-10% of a plasticizer, said film having incorporated therein a medicament, e.g., anesthetics, analgesics, anticaries agents, anti-inflammatories, antihistamines, antibiotics, antibacterials, fungistats, etc.

9 Claims, No Drawings

BIOADHESIVE EXTRUDED FILM FOR INTRA-ORAL DRUG DELIVERY AND PROCESS

BACKGROUND OF THE INVENTION

1. Field of the Invention

The present invention relates to a controlled-releasing medicament-containing preparation for intra-oral use, and is more especially concerned with such a preparation (and the process of using it) in the form of a very thin extruded thermoplastic film (which can be in single layer or laminated multi-layer form) having at least one bioadhesive layer containing 40–95% of a thermoplastic cellulose ether and 5–60% of a homopolymer of ethylene oxide which can adhere to the mucosa of the oral cavity. The extruded film drug delivery system of the present invention, which has incorporated therein the medicament to be dispensed, is so thin and flexible when wet as to be unobtrusive to the patient after it has been properly positioned and placed in the mouth.

2. Description of the Prior Art

Several systems have previously been described which pertain to the delivery of drugs into the oral cavity. These include:

1. Treatment of periodontal disease with tetracycline, chlorhexidine or metronidazole loaded into hollow cellulose acetate fibers. These fibers are packed in the periodontal pockets and provide controlled release of the drug to the infected area.
2. Cast films containing ethyl cellulose/propylene glycol with chlorhexidine or metronidazole for treatment of periodontal disease.
3. An orthodontic appliance with a hydroxyethyl methacrylate/methyl methacrylate copolymer (HEMA/MMA) matrix. Sodium fluoride is incorporated into the HEMA/MMA matrix to provide sustained fluoride release and enhanced anticaries activity. HEMA/MMA with fluoride may also be attached to the tooth in the form of a wafer-like tablet.
4. Silicone/ethyl cellulose/polyethylene glycol films containing sodium fluoride are applied as coatings on orthodontic bands or in chewing gum. Controlled release of fluoride and anticaries activity is claimed.

The above systems are discussed in the "The Compendium of Continuing Education" Vol VI, No. 1, January 1985 p. 27–36 review article "Controlled Drug Delivery: A New Means of Treatment of Dental Disease", by J. Max Goodson, D.D.S., Ph.D. of the Forsyth Dental Center. Other systems, described in GB patent application No. 2,042,888 and U.S. Pat. Nos. 4,292,299/4,226,848 (Teijin Ltd., Japan), use combinations of cellulosic and polyacrylate polymers. The preferred materials are hydroxypropyl cellulose ("Klucel") and a copolymer of acrylic acid ("Carbopol") that is administered in the form of thin tablets (discs), granules or powder. Other polymers that might be added are vinyl copolymers, polysaccharides, gelatin and collagen. U.S. Pat. No. 4,517,173 (Nippon Soda Co. Ltd, Japan) uses various celluloses in a multi-layered non-extruded cast film preparation.

Examples of prior art products currently on the market include ointments such as ORABASE* with Benzocaine (Squibb), Kenalog* (Triamcinolone Acetonide) in ORABASE* (Squibb) and Mycostatin* (Nystatin) ointment (Squibb).

The prior art products and delivery systems described above are useful but have the following disadvantages:

- Tablets, appliances, hollow fibers are "bulky" in the mouth, are difficult to keep in place and inconvenient to apply.
- Ethyl cellulose and/or silicone films do not adhere to mucosal tissue.
- Ointments (i.e., ORABASE*) have an unpleasant feel and do not last very long.
- Except for ORABASE*, all the foregoing systems require professional application to the tooth or periodontal pockets.

The bioadhesive film of the present invention alleviates many of the above problems. It may be applied easily by the consumer. It has very little or no mouthfeel, it has good adhesion to the mucosal tissues, and provides controlled release of the medicament.

OBJECT OF THE INVENTION

It is an object of this invention to provide an extruded film that is an effective and convenient intra-oral drug delivery system and method for applying and delivering controlled dosages of therapeutic agents into the oral cavity. This technology may also be extended for controlled drug delivery in skin care, gynecological applications, wound care and like uses.

SUMMARY OF THE INVENTION

The invention involves a pharmaceutically acceptable controlled-releasing medicament-containing extruded single or multi-layered thin film, capable of adhering to a wet mucous surface, comprising a water soluble or swellable polymer matrix bioadhesive layer which can adhere to a wet mucous surface and which bioadhesive layer consists essentially of 40–95% by weight of hydroxypropyl cellulose 5–60% of a homopolymer of ethylene oxide, 0–10% of a water-insoluble polymer selected from the group consisting of ethyl cellulose, propyl cellulose, polyethylene and polypropylene, and 2–10% of a plasticizer, said film having incorporated therein a pharmaceutically effective amount of said medicament.

The present invention is directed to an extruded single or multi-layered laminated thin (1–10 mils or 0.025–0.25 mm) film, composed of selected water soluble and/or insoluble polymers. Various therapeutic agents are incorporated into the film during manufacture which are useful for treatment of oral disorders (i.e., denture discomfort, caries, periodontal disease, aphthous ulcers, etc.).

The extruded film of the present invention must have at least one bioadhesive layer, but may also have a reservoir layer and/or an outer protective barrier membrane layer. The therapeutic agent may be incorporated into any or all of the layers. When properly formulated and fabricated, these films will adhere to wet mucosal surfaces, provide a protective barrier for injured tissue and deliver controlled/sustained dosages of medication to the infected areas. The film may be designed for localized drug delivery (i.e., the periodontal pocket, an aphthous lesion), or may allow diffusion of the drug into the oral cavity.

An example of a non-localized system would be the delivery of sodium fluoride for caries prevention. A single or laminated film with good adhesion to the tooth or mucosal tissue may be employed in which the fluoride release rates may be controlled by varying film solubilities and/or concentration of fluoride in a multi-layered film.

An example of a localized application of medication would be in the treatment of aphthous lesions. A laminated two layer film with benzocaine incorporated into the adhesive layer would directly contact the injured mucosa. The outer layer would consist of non-soluble/non-adhesive polymers that provide durability, protection and directs the delivery of benzocaine toward the lesion.

The film forming polymers that are useful in this invention are selected from pharmaceutical grade materials, or those that are considered generally regarded as safe (GRAS) as food additives. They include, hydroxypropyl cellulose, and polyethylene oxide homopolymers. Small amounts of other polymers, e.g., polyvinyl ether-maleic acid copolymers and the like may be used in small amounts as well, replacing a small portion of the other polymers. The above materials are either water soluble of swellable and are most useful in the bioadhesive layer of the film. Various non-soluble polymers may also be incorporated for modification of the film's permeability properties, such as ethyl cellulose, propyl cellulose, polyethylene, polypropylene and carboxymethylcellulose (free acid). By varying the ratios of the above polymers both the solubility and the adhesive properties of each layer of film may be controlled. Therefore, depending on the desired delivery rate, the type of disorder to be treated, the area to be treated and the medication being administered it is possible to custom design the film by selecting and blending various polymers. The final film product may also be fabricated into flexible tapes of varied thickness and width, "spots" of different sizes and shapes or other pre-shaped forms.

The medicaments and pharmaceutical agents set forth in the prior art discussed above may generally be delivered by the drug delivery system of the present invention. Usable medicaments are those which are capable of withstanding the heats and pressures generated in the extrusion process involved in making the film of the present invention. Preferred medicaments include:

Anesthetics/Analgesics-benzocaine, dyclonine HCl, phenol, aspirin, phenacetin, acetaminophen, potassium nitrate, etc.
Anticaries Agents-sodium fluoride, sodium monofluorophosphate, stannous fluoride, etc.
Anti-inflammatories-hydrocortisone acetate, triamcinolone acetonide, dipotassium, glycyrrhizinate, etc.
Antihistamines-chlorpheniramine maleate, ephedrine HCL, diphenhydramine HCL, etc.
Antibiotics-i.e., tetracycline, doxycycline hyclate, meclocycline, minocycline, etc.
Antibacterials-chlorhexidine, cetyl pyridinium chloride, benzethonium chloride, dequalinium chloride, silver sulfadiazene, phenol, thymol, hexedine, hexetidine, alexidine, etc.
Fungistats-nystatin, miconazole, ketoconazole, etc.

The above are illustrative examples of therapeutic agents that are used to treat oral disorders. The present invention is not to be limited to these specific materials especially where it is intended to deliver drug outside of the oral cavity e.g. to skin where other drugs may be desirable.

The film of the present invention has the advantage of being an extruded film, rather than a cast film. When a multi-layered film is involved, the different layers can be coextruded and then laminated together, or else each layer can be separately extruded one on the other, and then laminated together, so that the final multi-layered film is still very thin. The films of the present invention can be made in thicknesses of only 1–10 mils or 0.025–0.25 mm. The films are so thin that when placed in the mouth after they become wet they soon become unobtrusive, and hardly noticeable by most patients.

The film must always have a bioadhesive layer, which enables it to adhere to wet mucosal surfaces. The bioadhesive layer has 40–95% of hydroxypropyl cellulose, 5–60% of a homopolymer of ethylene oxide and 2–10% of a glycol plasticizer (all percents are % by weight).

The Hydroxypropyl cellulose (HPC), useful for purposes of the present invention is commercially available from Hercules, Inc. (Wilmington, DE) under the tradename KLUCEL*. Preferred grades include Klucel MF, with a molecular weight around 600,000 and having a viscosity of 4,000–6,000 cps (Brookfield) in 2 percent water solutions, or Klucel HF, having a molecular weight around 1,000,000 and viscosity of 1500–2500 cps in 1 percent water solution. In general, any HPC having a Molecular Weight above about 100,000 is useful for purposes of this invention.

The homopolymer of ethylene oxide useful for purposes of the present invention has a relatively high molecular weight, i.e., above 100,000 and preferably above 3,000,000. Such polymers are commercially available from various sources. The Union Carbide Corporation material, "Polyox WSR-301", which has a molecular weight of approximately 4,000,000–5,000,000 is most preferred for purposes of the present invention.

The "plasticizer" useful for purposes of the present invention are selected from glycols such as propylene glycol and polyethylene glycol; polyhydric alcohols such as glycerin and sorbitol; glycerol esters such as glycerol triacetate; fatty acid triglycerides such as NEOBEE* M-5 and MYVEROLS*; mineral oil; vegetable oils such as castor oil, etc.

For the uses for the present invention contemplated here, the plasticizer should be non-toxic. The purpose of the plasticizer is to improve polymer melt processing by reducing the polymer melt viscosity and to impart flexibility to the final product.

The preferred plasticizer for use in the present invention is either propylene glycol or polyethylene glycol (such as is available from Union Carbide Corporation as their series of Carbowaxes which runs from 200 to 600 molecular weight, of which we prefer to use Carbowax 400, which has a molecular weight of 400, average.

In addition to the polymers and plasticizer which are required ingredients of the films of the present invention, minor amounts of other non-essential but customary ingredients will often be used if desired, e.g., antioxidants, preservatives, flavors, colorants.

DETAILED DESCRIPTION

The following examples will serve to illustrate the present invention in greater detail. The units shown in the examples are parts by weight. The thickness of the layers is expressed in either mils (0.001 inches) or millimeters. For easy conversion, 4 mils is approximately equal to 0.1 mm.

EXAMPLE 1

Triple Layered Laminate Containing Sodium Fluoride for Anticaries Protection

This three layered film laminate is comprised of a "bioadhesive" layer, a sodium fluoride "reservoir"

layer and, an "outer protective barrier membrane" layer, in which the composition and thickness of each layer are as shown below:

| Ingredients | Bio-adhesive Layer (4 mils) (0.1 mm) | % w/w Reservoir Layer (1 mil) (0.025 mm) | Outer Protective Barrier Membrane Layer (1 mil) (0.025 mm) |
|---|---|---|---|
| Polyethylene oxide homopolymer (Union Carbide-Polyox* WSR-301) | 60.0 | — | — |
| Hydroxypropyl Cellulose (Hercules, Inc.-Klucel* MF) | 30.0 | 20.0 | 24.0 |
| Polyethylene (Allied Chemical-6A) (Low Density) | 5.0 | — | — |
| Propylene Glycol, U.S.P. | 3.0 | — | — |
| Polyethylene Glycol 400 (Union Carbide) | 2.0 | — | — |
| Ethyl Cellulose (Hercules, Inc.-N100F) | — | 59.0 | 69.6 |
| Caprylic/Capric Triglyceride (PVO Incorporated-Neobee M-5) | — | 5.0 | 6.0 |
| Sodium Fluoride, U.S.P. | — | 16.0 | 0.4 |
|  | 100.0 | 100.0 | 100.0 |

The process used to make the above laminate was:

a. Powder Blending-Each layer is made separately and all ingredients used therein except propylene glycol and Neobee M-5 (liquid plasticizers) are placed in a Patterson Kelley (PK) V-blender equipped with liquid addition capabilities. The ingredients which are all powders are blended for approximately 10-15 minutes while the liquid plasticizer is slowly added to the mix. Three separate powder blends are made, one for each layer.

b. Extrusion Process-A standard Johnson 2-½ inch vinyl/polyolefin extruder equipped with a single three stage screw was used to extrude the "powder blend". The temperature conditions for the water soluble powders are however quite different from those used for vinyls and polyolefins. The temperature (°C.) profile for the "reservoir" and "membrane layers" of the triple laminate was as follows:

| Barrel Zone 1 | 100 |
| Barrel Zone 2 | 125 |
| Barrel Zone 3 | 135 |
| Barrel Zone 4 | 145 |
| Barrel Zone 5 | 160 |
| Barrel Zone 6 | 170 |
| Adapter | 180 |
| Die Zone 1 | 180 |
| Die Zone 2 | 180 |
| Die Zone 3 | 180 |

The films which had a width of 18 inches, were extruded at approximately 20 feet/minute through a flat lipped die. The temperature profile for the "bioadhesive layer" was:

| Barrel Zone 1 | 125 |
| Barrel Zone 2 | 140 |
| Barrel Zone 3 | 165 |
| Barrel Zone 4 | 170 |
| Barrel Zone 5 | 185 |
| Barrel Zone 6 | 185 |
| Adapter | 185 |
| Die Zone 1 | 185 |
| Die Zone 2 | 185 |
| Die Zone 3 | 185 |

Each layer is extruded separately with the first layer extruded as a "free film". Successive layers are extruded onto each other and laminated by passing them through heated stainless steel rollers.

Test Results:

In vitro fluoride ion release studies were conducted on samples of the above described triple laminate film measuring 0.5 cm × 1.25 cm (0.625 cm$^2$) according to the following procedures:

The test sample is adhered to a glass slide by prewetting the film and placing the bioadhesive layer on the glass surface. The slide is then immersed in a beaker containing 100 ml of distilled water with continuous stirring. Five milliliter aliquots are withdrawn from the solution, at prescribed time intervals, and analyzed for fluoride content with an Orion Ionanlyzer equipped with a fluoride specific electrode. Release rates are then calculated from the data.

The results obtained indicated fluoride release rates in the order of 0.05–0.2 mgs/cm$^2$/hr for 24 hours. This falls within the desired range for maintaining constant low levels of fluoride in the mouth and enhanced anticaries activity. Release rates may be tailored to desired use levels by modification of the film composition and construction.

EXAMPLE 2

Single Layer Adhesive Film Containing Hydrocortisone Acetate (0.5%) As An Anti-Inflammatory Agent The composition of the film, which was 0.1 mm. thick, was as follows:

| Ingredients | % w/w |
|---|---|
| Ethylene Oxide Homopolymer (Polyox* WSR-301) | 59.4 |
| Hydroxypropyl Cellulose (Klucel* MF) | 30.0 |
| Polyethylene (AC-6A) | 5.0 |
| Propylene Glycol | 3.0 |
| Polyethylene Glycol 400 | 2.0 |
| Butylated Hydroxy Toluene (BHT) FCC (preservative) | 0.1 |
| Hydrocortisone Acetate | 0.5 |
|  | 100.0 |

The powder blending process and extruder conditions used were the same as those described in Example I for the "bioadhesive layer" of the sodium fluoride trilaminate. In vitro tests were performed on the above film and demonstrated a prolonged drug release pattern.

EXAMPLE 3

Single Layer Adhesive Film Containing Triamcinolone Acetonide (0.1%) As An Anti-Inflammatory The composition of the film, which was 0.1 mm. thick, was as follows:

| Ingredients | % w/w |
|---|---|
| Ethylene Oxide Homopolymer (Polyox WSR-301) | 59.9 |
| Hydroxypropyl Cellulose (Klucel MF) | 29.9 |

| Ingredients | % w/w |
|---|---|
| Polyethylene (AC-6A) | 5.0 |
| Propylene Glycol | 3.0 |
| Polyethylene Glycol 400 | 2.0 |
| BHT | 0.1 |
| Triamcinolone Acetonide | 0.1 |
| | 100.0 |

The powder blending process and extruder conditions used to make the film of this Example 3 were the same as those of the "bioadhesive layer" of Example I.

Other desired active medicament ingredients may be incorporated into the adhesive films of any of Examples 1-3 in place of the particular medicament used in said examples. These include Benzocaine (analgesic), Potassium nitrate (analgesic), Silver sulfadiazene (antimicrobial), Chlorhexidine (antimicrobial), miconazole nitrate (antifungal), Benzethonium chloride (antimicrobial), Tetracycline (antibiotic) and other similar therapeutic compounds.

EXAMPLE 4

Analgesic Films with Potassium Nitrate

This example shows 5 variations of the film having different solubilities, resulting in different release rates.

| | % w/w | | | | |
|---|---|---|---|---|---|
| Ingredients | 1 | 2 | 3 | 4 | 5 |
| Polyethylene oxide homopolymer (Polyox* WSR-301) | 23.75 | 57.00 | 55.00 | 55.00 | 57.00 |
| Hydroxypropyl Cellulose, N.F. (Klucel* HF) | 68.30 | — | — | — | — |
| Hydroxypropyl Cellulose, N.F. (Klucel* MF) | — | 28.40 | 29.90 | 22.40 | 22.40 |
| Ethyl Cellulose | — | 4.75 | 5.00 | 12.50 | 12.50 |
| Polyethylene Glycol 400 | 1.90 | 1.90 | 2.00 | 2.00 | 2.00 |
| Polyethylene Glycol 8000 | 0.95 | — | — | — | — |
| Propylene Glycol, U.S.P. | — | 2.85 | 3.00 | 3.00 | 3.00 |
| BHT, F.C.C. | 0.10 | 0.10 | 0.10 | 0.10 | 0.10 |
| Potassium Nitrate, F.C.C. | 5.00 | 5.00 | 5.00 | 5.00 | 3.00 |

The above ingredients are blended in a Patterson-Kelly powder blender equipped with liquid addition capabilities. The resulting powder blend is then extruded into film on a Killion or Johnson vinyl extruder using processing procedures similar to those of the bioadhesive layer of Example I.

EXAMPLE 5

Anesthetic Films with Benzocaine (Laminate)

This is an example of a two-layer laminate. The processing conditions used were similar to those of the bioadhesive layer and outer protective barrier membrane layer of Example I.

| A. | Inner medicated bioadhesive layer | |
|---|---|---|
| | Polyoxyethylene Homopolymer (Polyox* WSR-301) | 57.00 |
| | Hydroxypropyl Cellulose, N.F. (Klucel* MF) | 28.40 |
| | Polyethylene (AC-6A) | 4.75 |
| | Propylene Glycol, U.S.P. | 2.85 |
| | Polyethylene Glycol 400 | 1.90 |
| | BHT, F.C.C. | 0.10 |
| | Benzocaine, U.S.P. | 5.00 |
| | | 100.00 |
| B. | Outer protective/barrier layer | |
| | Hydroxypropyl Cellulose (Klucel* MF) | 78.00 |
| | Ethyl Cellulose | 20.00 |
| | Polyethylene Glycol 400 | 2.00 |
| | | 100.00 |

Part A was extruded on a Johnson extruder followed by subsequent extrusion and lamination of Part B to A.

Samples were applied to oral lesions, and provided profound anesthetic effects (lasting several hours) within minutes of application.

The identical two-layer laminate may also be made by coextruding the inner medicated bioadhesive layer (Part A) and the outer protective barrier layer (Part B) through separate die slots within a coextruder and laminating the two layers together.

EXAMPLE 6

Anesthetic Films with Phenol and Dyclonine HCl

Four variations of a single layer bioadhesive film were made as shown below:

| Ingredients | 1 | 2 | 3 | 4 |
|---|---|---|---|---|
| Polyethylene oxide homopolymer (Polyox* WSR-301) | 59.10 | 54.00 | 59.70 | 58.20 |
| Hydroxypropyl Cellulose (Klucel HF) | 29.45 | 26.91 | 29.75 | 29.00 |
| Ethyl Cellulose | 4.93 | 4.50 | 4.98 | 4.85 |
| Propylene Glycol, U.S.P. | 2.96 | 2.70 | 2.99 | 2.91 |
| Polyethylene Glycol 400 | 1.97 | 1.80 | 1.99 | 1.94 |
| BHT, F.C.C. | 0.09 | 0.09 | 0.09 | 0.10 |
| Phenol, U.S.P. | 1.50 | — | — | — |
| Dyclonine HCl | — | 10.00 | 0.50 | 3.00 |

Following the procedures for the bioadhesive layer of Example I, the powders were blended in P-K blender equipped with liquid addition capabilities. Resulting powders were extruded on a Killion laboratory-sized extruder.

EXAMPLE 7

Silver Sulfadiazene Films-Antimicrobial

Three different single-layered bioadhesive films containing 1.0% 0.5% and 0.5% respectively of silver sulfadiazene (SSD) were prepared on a heated Carver laboratory press (designed to simulate extruded conditions) as shown below.

| | % w/w | |
|---|---|---|
| Ingredients | A | B |
| Polyethylene oxide homopolymer (Polyox* WSR-301) | 60.00 | 60.00 |
| Hydroxypropyl Cellulose (Klucel* HF) | 28.9 | 29.4 |
| Polyethylene (AC-6A) | 5.0 | 5.0 |
| Propylene Glycol, U.S.P. | 3.0 | 3.0 |
| Polyethylene Glycol 400 | 2.0 | 2.0 |
| BHT, F.C.C. | 0.1 | 0.1 |
| Silver Sulfadiazine | 1.0 | 0.5 |
| | 100.0 | 100.0 |

Effects on wound repair and activity against *Staphylococcus aureus* were evaluated in the guinea pig model. Full-thickness excisions were inoculated with $3.8 \times 10^5$ organisms, (*Staph. aureus*) and wound surface microbiology samples taken 10 minutes and 24 hours after treatment. Test films were placed on the wound and covered with BIOCLUSIVE* Transparent Dressings secured with elastic tape. Wound contraction was measured over an eight-day period using OPTOMAX* Computer-Assisted Image Analysis. The three films tested were the following:

A. 1.0% Silver Sulfadiazene, 125° C./2 minutes/4 tons
B. 0.5% Silver Sulfadiazene, 125° C./2 minutes/4 tons
C. 0.5% Silver Sulfadiazene, 150° C./3 minutes/4 tons
SILVADENE Cream and an untreated occluded control. The results indicated that:

1. SILVADENE* treated wounds significantly inhibited full-thickness wound contraction.
2. Film A, B and C inhibited wound contraction relative to that of BIOCLUSIVE* dressed wounds.
3. The three SSD films each permitted substantially faster wound contraction than that of wounds treated daily with SILVADENE* cream.
4. All films were very active against S. aureus 24 hours after inoculation.

The films may be scaled up by using an extruder. This example demonstrates the feasibility of such a film to perform its intended purpose. Use of a press for larger samples would result in a non-uniform and lower-quality film than an extruded film.

Based on the above findings, the films were very effective antibacterial agents, while mildly inhibiting wound contraction. They offer clinicians a convenient and more effective delivery system for antimicrobials which can be place in wounds beneath any dressing or can be laminated to any acceptable dressing face.

What is claimed is:

1. A pharmaceutically acceptable controlled-releasing medicament-containing extruded single or multi-layered thin film, capable of adhering to a wet mucous surface, comprising a water soluble or swellable polymer matrix bioadhesive layer which can adhere to a wet mucous surface and which bioadhesive layer consists essentially of 40-95% by weight of a hydroxypropyl cellulose having a molecular weight above 100,000, 5-60% of a homopolymer of ethylene oxide having a molecular weight from 3,000,000 to 5,000,000, 0-10% of a water-insoluble polymer selected from the group consisting of ethyl cellulose, propyl cellulose, polyethylene and polypropylene, and 2-10% of a plasticizer, said film having incorporated therein a pharmaceutically effective amount of said medicament.

2. The extruded film of claim 1, made in a form which is so thin and flexible when wet as to be unobtrusive to the patient when properly positioned and placed in the patients mouth.

3. The extruded film of claim 2 having a thickness no greater than 0.25 millimeters.

4. The extruded film of claim 1, in single layer form, which also contains up to 10% by weight of a non-soluble polymer selected from the group consisting of ethyl cellulose, polyethylene, polypropylene and carboxymethyl cellulose free acid.

5. The extruded film of claim 1, in multi-layer laminated form, which is addition to the bioadhesive layer also contains a reservoir layer in which at least a major portion of the medicament is contained.

6. The extruded multi-layer film of claim 5 in which the reservoir layer consists essentially of a polymer matrix comprised of both a water soluble or swellable polymer and a non-water soluble polymer selected from the group consisting of ethyl cellulose, propyl cellulose, polyethylene and polypropylene, and also hydroxypropyl cellulose.

7. The extruded film of claim 1 in multi-layer laminated form, which in addition to the bioadhesive layer also contains an outer protective-barrier membrane layer.

8. The extruded multi-layer film of claim 7 in which the outer protective-barrier membrane layer is thinner than the bioadhesive layer, and said outer protective barrier layer consists essentially of a polymer matrix of a major proportion of a non-water-soluble polymer selected from the group consisting of ethyl cellulose, propyl cellulose, polyethylene and polypropylene, and a minor proportion of hydroxypropyl cellulose.

9. The extruded multi-layer film of claim 1 in the form of a triple layered laminate containing sodium fluoride for anticaries protection having the following composition:

| Ingredients | Bioadhesive Layer (0.1 mm) | % w/w Reservoir Layer (0.025 mm) | Outer Protective Barrier Membrane Layer (0.025 mm) |
| --- | --- | --- | --- |
| Polyethylene oxide homopolymer (MW 3,000,000 minimum) | 60.0 | — | — |
| Hydroxypropyl Cellulose (MW 1,000,000) | 30.0 | 20.0 | 24.0 |
| Polyethylene (Low Density) | 5.0 | — | — |
| Propylene Glycol, U.S.P. | 3.0 | — | — |
| Polyethylene Glycol (MW 400) | 2.0 | — | — |
| Ethyl Cellulose | — | 59.0 | 69.6 |
| Caprylic/Capric Triglyceride | — | 5.0 | 6.0 |
| Sodium Fluoride | — | 16.0 | 0.4 |
| | 100.0 | 100.0 | 100.0 |

* * * * *